United States Patent [19]

Nohr et al.

[11] Patent Number: 5,336,707
[45] Date of Patent: Aug. 9, 1994

[54] SURFACE SEGREGATION THROUGH THE USE OF A BLOCK COPOLYMER

[75] Inventors: Ronald S. Nohr, Roswell; John G. MacDonald, Decatur, both of Ga.

[73] Assignee: Kimberly-Clark Corporation, Neenah, Wis.

[21] Appl. No.: 972,678

[22] Filed: Nov. 6, 1992

[51] Int. Cl.⁵ .................. C08K 5/54; C08L 53/00; C08L 83/12
[52] U.S. Cl. ................... 524/265; 524/261; 524/269; 524/505; 524/588
[58] Field of Search ............ 524/261, 265, 269, 505, 524/588

[56] References Cited

U.S. PATENT DOCUMENTS

| | | | |
|---|---|---|---|
| Re. 32,514 | 10/1987 | Steklenski | 524/32 |
| 3,491,137 | 1/1970 | Zaweski et al. | 524/265 |
| 3,502,763 | 3/1970 | Hartmann | 264/210 |
| 3,723,402 | 3/1973 | Owen et al. | 524/265 |
| 4,446,090 | 5/1984 | Lovgren et al. | 264/211 |
| 4,535,113 | 8/1985 | Foster et al. | 524/262 |
| 4,578,414 | 3/1986 | Sawyer et al. | 524/310 |
| 4,689,362 | 8/1987 | Dexter | 525/106 |
| 4,857,251 | 8/1989 | Nohr et al. | 264/103 |
| 4,920,168 | 4/1990 | Nohr et al. | 524/265 |
| 4,923,914 | 5/1990 | Nohr et al. | 524/265 |
| 4,931,492 | 6/1990 | Foster et al. | 524/265 |
| 5,057,262 | 1/1991 | Nohr et al. | 264/237 |
| 5,120,888 | 6/1992 | Nohr et al. | 524/265 |

FOREIGN PATENT DOCUMENTS 0197650  9/1986  Japan ................ 524/265

Primary Examiner—Paul R. Michl
Assistant Examiner—Peter Szekely

[57] ABSTRACT

A surface-segregatable, melt-extrudable thermoplastic composition is provided which includes (A) a thermoplastic polypropylene-polyethylene block copolymer in which the polyethylene blocks constitute from about 1 to about 10 percent by weight of the copolymer and (B) a defined trisiloxane polyether additive having a molecular weight of from about 350 to about 1,400, which additive is present in an amount of from about 0.1 to about 5 percent by weight, based on the amount of thermoplastic block copolymer. The use of the block copolymer unexpectedly permits the use of significantly reduced amounts of additive while still providing nonwoven webs which are immediately wettable and which do not become significantly less wettable over time.

7 Claims, 5 Drawing Sheets

SURFACE SEGREGATION THROUGH THE USE OF A BLOCK COPOLYMER

BACKGROUND OF THE INVENTION

The present invention relates to improved surface segregation of polysiloxane polyethers contained in a thermoplastic composition which is melt extruded to form fibers or nonwoven webs. Such improvement results from the use of a polypropylene-polyethylene block copolymer as the thermoplastic polymer component.

Surface-segregatable, melt-extrudable thermoplastic compositions are described in U.S. Pat. No. 4,923,914, SURFACE-SEGREGATABLE, MELT-EXTRUDABLE THERMOPLASTIC COMPOSITION, which issued in the names of Ronald S. Nohr and J. Gavin MacDonald. The patent describes a surface-segregatable, melt-extrudable thermoplastic composition which includes at least one thermoplastic polymer and at least one additive having at least two moieties, A and B, in which:

(A) the additive is compatible with the polymer at melt extrusion temperatures but is incompatible at temperatures below melt extrusion temperatures, but each of moiety A and moiety B, if present as separate compounds, would be incompatible with the polymer at melt extrusion temperatures and at temperatures below melt extrusion temperatures;

(B) moiety B has at least one functional group which imparts to the additive at least one desired characteristic;

(C) the molecular weight of the additive is in the range of from about 400 to about 15,000; and (D) the weight ratio of the polymer to the additive is in the range of from about 1 to about 1,000;

with the proviso that the additive cannot be a compound having the general formula, in which each R independently is a monovalent organic group selected from the group consisting of alkyl groups; $R^1$ is a monovalent organic group containing at least one ethyleneoxy group, vicinal epoxy group, or amino group; and a and b, which can be the same or different, each have a value of at least 1. In desired embodiments, the additive is a siloxane-containing compound, and one of the desired characteristics is wettability by water when the polymer is inherently hydrophobic.

The compositions described in that patent are particularly useful for the formation of nonwoven webs by such melt-extrusion processes as meltblowing, coforming, and spunbonding. Upon being melt-extruded, such compositions result in a fiber (or film) having a differential, increasing concentration of the additive from the center to the surface thereof, such that the concentration of additive toward the surface of the fiber is greater than the average concentration of additive in the more central region of the fiber and imparts to the surface of the fiber at least one desired characteristic which otherwise would not be present.

When the additive was a siloxane-containing compound and the desired characteristic was water-wettability, the resulting nonwoven webs often became less wettable over time and frequently reverted to a nonwettable state. This loss of wettability, or aging, was accelerated when the polymer composition contained titanium dioxide. However, the absence of titanium dioxide did not prevent the aging which typically was complete within a matter of days.

A subclass of the additives encompassed by U.S. Pat. No. 4,923,914 subsequently was discovered which permitted the preparation of wettable nonwoven webs which remained wettable for at least about two years at ambient temperature. Such subclass is described and claimed in application Ser. No. 07/566,589, entitled SURFACE-SEGREGATABLE COMPOSITIONS AND NONWOVEN WEBS PREPARED THEREFROM and filed Aug. 13, 1990 in the names of Ronald S. Nohr and J. Gavin MacDonald.

Application Ser. No. 07/566,589 provides a surface-segregatable, melt-extrudable thermoplastic composition which includes at least one thermoplastic polyolefin and at least one additive having the general formula, in which:

(a) $R_1$–$R_9$ are independently selected monovalent $C_1$–$C_3$ alkyl groups;

(b) $R_{10}$ is hydrogen or a monovalent $C_1$–$C_3$ alkyl group;

(c) m represents an integer of from 1 to about 4;

(d) n represents an integer of from 0 to about 3;

(e) the sum of m and n is in the range of from 1 to about 4;

(f) p represents an integer of from 0 to about 5;

(g) x represents an integer of from 1 to about 10;

(h) y represents an integer of from 0 to about 5;

(i) the ratio of x to y is equal to or greater than 2;

(j) the additive has a molecular weight of from about 350 to about 1,400; and (k) the additive is present in an amount of from about 0.1 to about 5 percent by weight, based on the amount of thermoplastic polyolefin.

A particularly desirable subclass of the additives of application Ser. No. 07/566,589 includes trisiloxane polyethers, i.e., compounds having the above general formula in which m is 1 and n is 0.

It now has been discovered that the amounts of a particular group of trisiloxane polyethers in a thermoplastic composition can be significantly reduced without notably adversely affecting either the wettability of nonwoven webs prepared from such compositions or their long-term wettability characteristics. Moreover, the webs are immediately wettable without the need for a post-formation treatment of any kind.

SUMMARY OF THE INVENTION

It therefore is an object of the present invention to provide a surface-segregatable, melt-extrudable thermoplastic composition which, upon melt-processing to give a nonwoven web, produces fibers which are wettable by water and which remain wettable over time.

Another object of the present invention is to provide a wettable nonwoven web which remains wettable over time.

A further object of the present invention is to provide a disposable absorbent product, at least one component of which is a wettable nonwoven web which remains wettable over time.

These and other objects will be apparent to those having ordinary skill in the art from a consideration of the specification and claims which follow.

Accordingly, the present invention provides a surface-segregatable, melt-extrudable thermoplastic composition which includes:

(A) a thermoplastic polypropylene-polyethylene block copolymer in which the polyethylene blocks constitute from about 1 to about 10 percent by weight of the copolymer and (B) an additive having the general formula, in which:
(1) $R_1-R_7$ are independently selected monovalent $C_1-C_3$ alkyl groups;
(2) $R_8$ is hydrogen or a monovalent $C_1-C_3$ alkyl group;
(3) p represents an integer of from 0 to about 5;
(4) x represents an integer of from 1 to about 15;
(5) the additive has a molecular weight of from about 350 to about 1,400; and
(6) the additive is present in an amount of from about 0.1 to about 5 percent by weight, based on the amount of thermoplastic block copolymer.

The present invention also provides a nonwoven web comprising fibers prepared from the above-described composition, which web remains wettable for at least two years at ambient temperature, as well as a disposable absorbent product containing such nonwoven web. Examples of disposable absorbent products for which the nonwoven webs of the present invention are particularly well-suited are disposable diapers, feminine care products such as sanitary napkins and tampons, wipes, and the like.

DETAILED DESCRIPTION OF THE INVENTION

The use herein of the term "surface-segregatable" is consistence with its use in U.S. Pat. No. 4,923,914. Upon melt-extruding a composition of the present invention to form fibers, there is in such a fiber a differential, increasing concentration of the additive from the center to the surface thereof. The concentration of additive at or near the surface of the fiber is sufficient to render the normally hydrophobic polyolefin wettable by water, or hydrophilic. Unless stated otherwise, the term "hydrophilic" will be used herein to mean water-wettable. Thus, there is a controlled migration or segregation of additive toward the surface of the fiber which results in a controllable, differential concentration of additive in the fiber. Because the concentration of additive in the center portion of the fiber typically will vary nonlinearly from the concentration of the additive at or near the surface, this concentration difference is referred to herein as a differential concentration.

Without wishing to be bound by theory, the surface segregation phenomenon described in U.S. Pat. No. 4,923,914 now appears to be best explained on the basis of micelle formation. Thus, a relatively low molecular weight additive is miscible with the polymer at melt extrusion temperatures, forming an unstable emulsion characterized by metastable micellular structures. Upon extrusion, during which a rapid increase in shear rate is experienced, the additive is believed to break free from the metastable micelle "aggregate" and molecularly diffuse to the fiber surface. Such diffusion is driven in part by both a loss of additive compatibility and a potential drop in interfacial free energy. In light of the unexpected results described herein, it appears that the presence of polyethylene blocks enhances the loss of additive compatibility. This increases the rate of migration which forces more additive molecules to the surface before fiber solidification stops additive migration. Consequently, significantly lower additive levels are required to give wettable fiber surfaces.

The term "melt-extrudable" is equivalent to "melt-processable" and is not intended to be limited in any way. That is, the term is intended to encompass the use of the composition in any melt-extrusion process which is or may be employed to prepare nonwoven webs, provided the process meets the limitations imposed by the claims. Thus, the term includes the use of the composition in meltblowing, spunbonding, coforming, and the like.

The composition of the present invention is composed primarily of a thermoplastic polymer component and an additive. The thermoplastic polymer component is a polypropylene-polyethylene block copolymer in which the polyethylene blocks constitute from about 1 to about 10 percent by weight of the copolymer. In particular, the polyethylene blocks constitute from about 1 to about 6 percent by weight of the copolymer.

The composition of the present invention also must contain at least one additive having the general formula, in which:
(1) $R_1$-$R_7$ are independently selected monovalent $C_1$-$C_3$ alkyl groups;
(2) $R_8$ is hydrogen or a monovalent $C_1$-$C_3$ alkyl group;
(3) p represents an integer of from 0 to about 5;
(4) x represents an integer of from 1 to about 15;
(5) the additive has a molecular weight of from about 350 to about 1,400; and
(6) the additive is present in an amount of from about 0.1 to about 5 percent by weight, based on the amount of thermoplastic block copolymer.

In desired embodiments, each of $R_1$-$R_7$ is a methyl group. In other desired embodiments, $R_8$ is either hydrogen or a methyl group. In yet other desired embodiments, p is either 1 or 2, but most desirably is 2. In yet other desired embodiments, x is 7 or 8.

While the additive molecular weight can vary from about 350 to about 1,400, it desirably will not exceed about 850. More desirably, the weight average molecular weight will be in the range of from about 350 to about 700.

While the additive can be either a liquid or a solid, a liquid is desirable. It also is desired that a liquid additive have a surface tension which is less than that of virgin polymer; the lower surface tension assures that the additive will be more likely to completely "wet" or cover the surface of the fiber or film as the segregation process proceeds to completion, especially under conditions favoring a large concentration differential.

In general, the additive will be present in an amount of from about 0.1 to about 5 percent by weight, based on the amount of thermoplastic block copolymer. As a practical matter, additive levels of from about 0.1 to about 3 percent by weight are particularly desired. More particularly, additive levels will be in the range of from about 0.2 to about 1 percent by weight.

The term "additive" is used broadly herein to encompass the use of more than one additive in a given composition, i.e., a mixture of two or more additives. Moreover, it should be appreciated by those having ordinary skill in the art that additives as defined herein typically are not available as pure compounds. Thus, the presence of impurities or related materials which may not come within the general formula given above for the additives does remove any given material from the spirit and scope of the present invention. For example, the preparation of additives useful in the present invention typically results in the presence of free polyether. The presence of such free polyether is not known to have deleterious effects, although it may be necessary to increase the amount of additive to compensate for the presence of free polyether. As a practical matter, it is desired that the amount of free polyether present in any additive be no more than about 30 percent by weight. More desirably, the amount of free polyether present in an additive will be no more than about 20 percent by weight.

A nonwoven web in general is readily prepared from a composition of the present invention by either of two methods. The first method involves:
(A) melting a mixture which includes a thermoplastic block copolymer and an additive as already defined;
(B) forming fibers by extruding the resulting melt through a die at a shear rate of from about 50 to about 30,000 sec$^{-1}$ and a throughput of no more than about 5.4 kg/cm/hour;
(C) drawing the fibers; and
(D) collecting the fibers on a moving foraminous surface as a web of entangled fibers.

In the first step, a mixture of the thermoplastic block copolymer and an additive is melted. This typically is done in an extruder which is an integral part of the apparatus used to form fibers.

Fibers then are formed by extruding the molten mixture through a die. Although the nature of the die is not known to be critical, it most often will have a plurality of orifices arranged in one or more rows extending the full machine width. Such orifices may be circular or noncircular in cross-section. The fibers extruded may be either continuous or substantially continuous.

In general, the shear rate will be in the range of from about 50 to about 30,000 sec$^{-1}$. Desirably, the shear rate will be in the range of from about 150 to, about 5,000 sec$^{-1}$ and more desirably from about 300 to about 2,000 sec$^{-1}$.

Throughput is of importance because it affects the time the newly formed fibers are in a sufficiently molten or fluid state to allow migration or segregation of the additive toward the newly formed surfaces, even though throughput also affects the shear rate.

Throughput typically will be in the range of from about 0.01 to about 5.4 kg/cm/hour. Desirably, throughput will be in the range from about 0.1 to about 4.0 kg/cm.hour. The throughput more desirably will be in the range of from about 0.5 to about 2.5 kg/cm/hour.

As used herein, the phrase "molten state" does not necessarily mean "flowable". Rather, the term is used to denote a condition of the thermoplastic composition in which the additive molecules still are capable of migrating or segregating to the surface of the newly formed fiber. Thus, the term is somewhat imprecise and not readily subject to accurate measurement. Consequently, this composition fluidity factor preferentially is described or accounted for by the term "throughput".

The fibers then are drawn, typically by entraining them in a fluid stream having a sufficiently high velocity. When continuous fibers are produced, the fibers first are cooled in a quenching fluid which usually is low pressure air. The fluid stream which draws the fibers, usually air, can be a stream of high velocity air separate from the quenching fluid, or it can be a portion of the quenching fluid which is accelerated by passage into a narrow nozzle. In the production of substantially continuous fibers, on the other hand, the fluid stream usually is a heated, high velocity stream of air which draws the fibers while they are in an at least partially molten or softened state.

The drawn fibers then are collected on a moving foraminous surface as a web of entangled fibers. The foraminous surface can be, by way of example only, a revolving drum or a continuous belt or wire screen; the latter is most commonly used on commercial-scale equipment.

In general, the steps of melting, forming, drawing, and collecting are carried out as described in such processes as meltblowing, coforming, spunbonding, and the like. By way of illustration only, such processes are exemplified by the following references which are incorporated herein by reference:

(a) meltblowing references include, by way of example, U.S. Pat. Nos. 3,016,599 to R. W. Perry, Jr., 3,704,198 to J. S. Prentice, 3,755,527 to J. P. Keller et al., 3,849,241 to R. R. Butin et al., 3,978,185 to R. R. Butin et al., and 4,663,220 to T. J. Wisneski et al. See, also, V. A. Wente, "Superfine Thermoplastic Fibers", *Industrial and Engineering Chemistry*, Vol. 48, No. 8, pp. 1342–1346 (1956); V. A. Wente et al., "Manufacture of Superfine Organic Fibers", Navy Research Laboratory, Washington, D.C., NRL Report 4364 (111437), dated May 25, 1954, U. S. Department of Commerce, Office of Technical Services; and Robert R. Butin and Dwight T. Lohkamp, "Melt Blowing—A One-Step Web Process for New Nonwoven Products", *Journal of the Technical Association of the Pulp and Paper Industry*, Vol. 56, No.4, pp. 74–77 (1973);

(b) coforming references (i.e., references disclosing a meltblowing process in which fibers or particles are comingled with the meltblown fibers as they are formed) include U.S. Pat. Nos. 4,100,324 to R. A. Anderson et al. and 4,118,531 to E. R. Hauser; and (c) spunbonding references include, among others, U.S. Pat. Nos. 3,341,394 to Kinney, 3,655,862 to Dorschner et al., 3,692,618 to Dorschner et al., 3,705,068 to Dobo et at., 3,802,817 to Matsuki et al., 3,853,651 to Porte, 4,064,605 to Akiyama et al., 4,091,140 to Harmon, 4,100,319 to Schwartz, 4,340,563 to Appel and Morman, 4,405,297 to Appel and Morman, 4,434,204 to Hartman et al., 4,627,811 to Greiser and Wagner, and 4,644,045 to Fowells.

It may be noted at this point that if continuous fibers are formed, such as by a spunbonding process, the resulting web usually must be bonded by any known means in order to give the web sufficient integrity to permit its removal from the foraminous support. As a practical matter, however, the web will be pattern bonded by the application of heat and pressure. Desirably, such application of heat and pressure will be in the ranges of from about 80° C. to about 180° C. and from about 150 to about 1,000 pounds per linear inch (59–178 kg/cm), respectively. More desirably, a pattern having from about 10 to about 250 bonds/inch² (1–40 bonds/cm²) covering from about 5 to about 30 percent of the web surface area will be employed.

Such pattern bonding is accomplished in accordance with known procedures. See, for example, U.S. Des. No. 239,566 to Vogt, U.S. Des. No. 264,512 to Rogers, U.S. Pat. No. 3,855,046 to Hansen et al., and U.S. Pat. No. 4,493,868, Supra, for illustrations of bonding patterns and a discussion of bonding procedures.

The second general method for preparing a nonwoven web from a composition of the present invention involves:

(A) melting a mixture which comprises a thermoplastic block copolymer and an additive as already defined;

(B) forming continuous fibers by extruding the resulting melt through a die at a shear rate of from about 50 to about 30,000 sec$^{-1}$ and a throughput of no more than about 5.4 kg/cm/hour;

(C) drawing the continuous fibers;

(D) collecting the continuous fibers into a tow;

(E) cutting the tow into staple fibers;

(F) laying the staple fibers onto a moving foraminous surface as a web of entangled fibers; and (G) bonding the resulting nonwoven web.

Each of the foregoing steps also is carried out by any of several means which are well known to those having ordinary skill in the art. If desired, individual continuous fibers can be false twisted before collecting them as a tow. Moreover, the tow can be crimped before cutting into staple-length fibers. Although the staple fibers can be laid onto the moving foraminous support by any known means, they desirably will be either air-laid or wet-laid.

Finally, the bonding of the resulting nonwoven web can be by any known means, as described hereinabove. Again, however, the web desirably will be pattern bonded by the application of heat and pressure, also as already described.

The present invention is further described by the examples which follow. Such examples, however, are not to be construed as limiting in any way either the spirit or scope of the present invention. In the examples, all temperatures are in degrees Celsius and all parts are by weight unless stated otherwise.

EXAMPLES 1–12

Preparation of Spunbonded Nonwoven Webs

Spunbonded nonwoven webs were prepared on a pilot-scale apparatus essentially as described in U.S. Pat. No. 4,340,563, which is incorporated herein by reference. Examples 1–8 involved compositions of the present invention. Examples 9–12 are controls, in which the polymer was a polypropylene homopolymer.

The thermoplastic block copolymers employed were Escorene 9325 and Escorene 9355 (Exxon Chemical Americas, Houston, Tex. 77079). Escorene 9325 is a polypropylene-polyethylene block copolymer containing 1.3 percent by weight polyethylene blocks, based on the total weight of the copolymer. Escorene 9355 is a polypropylene-polyethylene block copolymer containing 3 percent by weight polyethylene blocks.

The polypropylene homopolymer employed in Examples 9–12 was Escorene 3445 (Exxon Chemical Americas, Houston, Tex. 77079). According to the manufacturer, the polymer has a density of 0.90 g/cc and a melt flow rate of 35 g/10 minutes.

The additive in every case was a trisiloxane polyether having the general formula, Based on gel permeation chromatography studies in tetrahydrofuran at 50° C. (American Polymer Standards Corporation, Mentor, Ohio) relative to PDMS standards, the following average molecular weights were calculated:

Weight-average molecular weight: 600
Number-average molecular weight: 543
Z-average molecular weight: 644
Polydispersity: 1.1

Additive was incorporated into either the block copolymer or the polypropylene at levels ranging from 0.2 to 1.25 percent by weight. The polymer and additive were simply mixed mechanically before introducing the mixture to the feed hopper of the extruder. Typically, a standard portable cement mixer was charged with 50 pounds of the polymer in pellet form. The mixer then was started and charged with the desired amount of additive. Mixing was allowed to continue for 20 minutes, after which time the mixture was removed from the mixer and stored in plastic-lined boxes.

The more significant process variables generally were as follows:

| | |
|---|---|
| extruder temperature, | 200–233°; |
| melt inlet temperature, | 233–236°; |
| throughput, | 39 kg per hour; |
| spin head temperature, | 226–233°; |
| pump block temperature, | 231–236°; |
| pack temperature, | 237–243°; |
| pack pressure, | 200 psig; and |
| melt temperatrue, | 223–224° |

In each case, webs were obtained which had a basis weight of about 68 g/m$^2$.

The wettability of each web immediately after its formation was estimated by placing a drop of water on the web and measuring the time required for complete penetration of the water drop into the web. Each web was tested with a minimum of five drops of water placed in five different locations. A web was considered immediately wettable if all of the drops wet the web within three seconds.

Table 1 summarizes the webs obtained by additive level and polymer type and gives the wettability test results and silicon-carbon (Si/C) ratios as determined by electron spectroscopy for chemical analysis (ESCA). The ESCA data were obtained by Surface Science laboratories, Inc., Mountain View, Calif., essentially as described in U.S. Pat. No. 4,923,914.

TABLE 1

| | | Summary of Results | | | |
|---|---|---|---|---|---|
| Example | Polymer Type | % PE Blocks | % Additive | Wettable | Si/C Ratio |
| 1 | 9325 | 1.3 | 0.2 | No | 0.005 |
| 2 | 9355 | 3 | 0.2 | Yes | 0.020 |
| 3 | 9325 | 1.3 | 0.3 | Yes | 0.019 |
| 4 | 9355 | 3 | 0.3 | Yes | 0.043 |
| 5 | 9325 | 1.3 | 0.4 | Yes | 0.036 |
| 6 | 9355 | 3 | 0.4 | Yes | 0.075 |
| 7 | 9325 | 1.3 | 0.5 | Yes | 0.048 |
| 8 | 9355 | 3 | 0.5 | Yes | 0.065 |
| 9 | 3445 | 0 | 0.4 | No | 0.008 |
| 10 | 3445 | 0 | 0.75 | Yes | 0.013 |
| 11 | 3445 | 0 | 1.0 | Yes | 0.023 |
| 12 | 3445 | 0 | 1.25 | Yes | 0.039 |

A careful study of the data in Table 1 makes it clear that the use of a polypropylene-polyethylene block copolymer as the thermoplastic polymer component of a melt-extrudable composition gives unexpectedly high levels of silicon at or near the surfaces of the fibers prepared from such compositions. Based on prior experience with polypropylene homopolymers, the high levels of silicon observed with the block copolymers were surprising, especially in view of the three- to four-fold increases in surface silicon concentrations as measured by ESCA. A high level of silicon is indicative of a high level of additive at or near the surfaces of the fibers which in turn results in the immediate wettability of the nonwoven webs.

Based on the control webs, it appears that an Si/C ratio of at least about 0.010 is required for immediate wettability. Regardless of the polymer type, webs having Si/C ratios of 0.005 and 0.008 were not immediately wettable, whereas webs having an Si/C ratio of 0.013 or higher were immediately wettable. The use of a polypropylene-polyethylene block copolymer as described herein achieved higher levels of additive at or near the surfaces of the fibers with significantly lower levels of additive than can be achieved with homopolymer alone. Remarkably, additive levels in polypropylene-polyethylene block copolymers which were only about one-fourth to one-third of the levels in polypropylene gave similar Si/C ratios. Thus, the presence of polyethylene blocks appears to have a synergistic effect which permits reducing the amount of additive in the composition.

In order to assist in the visualization and appreciation of these remarkable and unexpected results, a number of graphs have been prepared and included as drawings.

Figure 1:
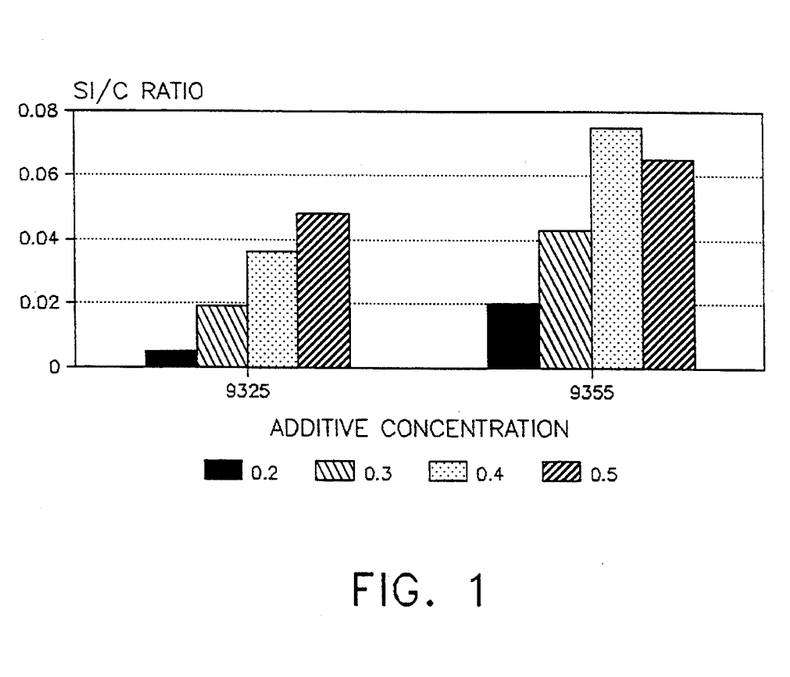
FIG. 1 is a bar graph illustrating the effect of additive concentration on silicon/carbon (Si/C) ratios at the surfaces of the fibers of nonwoven webs prepared in accordance with the present invention with two thermoplastic block copolymers having different levels of polyethylene blocks.

FIG. 1 is a bar graph illustrating the effect of additive concentration on silicon/carbon (Si/C) ratios at the surfaces of the fibers of nonwoven webs prepared in accordance with the present invention with two thermoplastic block copolymers having different levels of polyethylene blocks. The chart was prepared from the data in Table 1 for Examples 1–8, inclusive; the data were grouped by polymer type to illustrate the effect of additive concentration for each of the two block copolymers employed.

Figure 2:
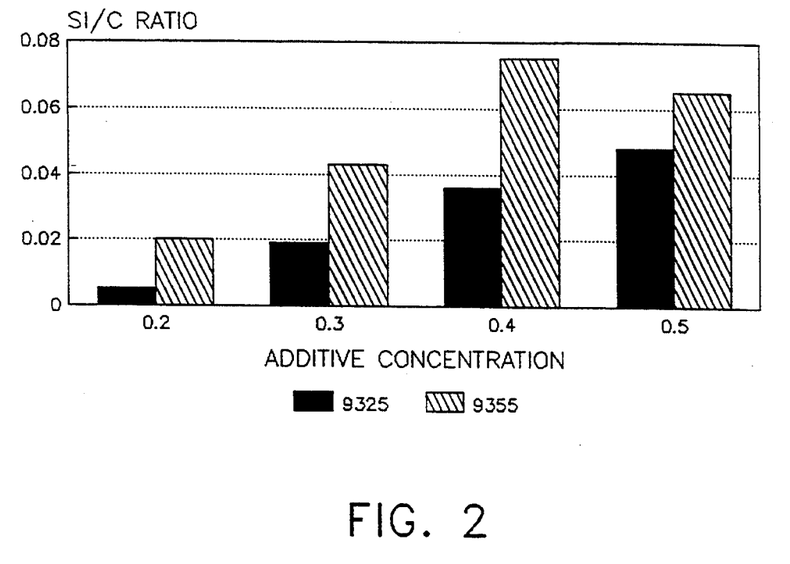
FIG. 2 is a bar graph illustrating the effect of polyethylene block content at given additive concentrations on Si/C ratios at the surfaces of the fibers of nonwoven webs prepared in accordance with the present invention.

FIG. 2 is a bar graph illustrating the effect of polyethylene block content at given additive concentrations on Si/C ratios at the surfaces of the fibers of nonwoven webs prepared in accordance with the present invention. Although the graph also was prepared from the data in Table 1 for Examples 1–8, the data were grouped by additive level to emphasize the effect of polyethylene block level on Si/C ratios.

Figure 3:
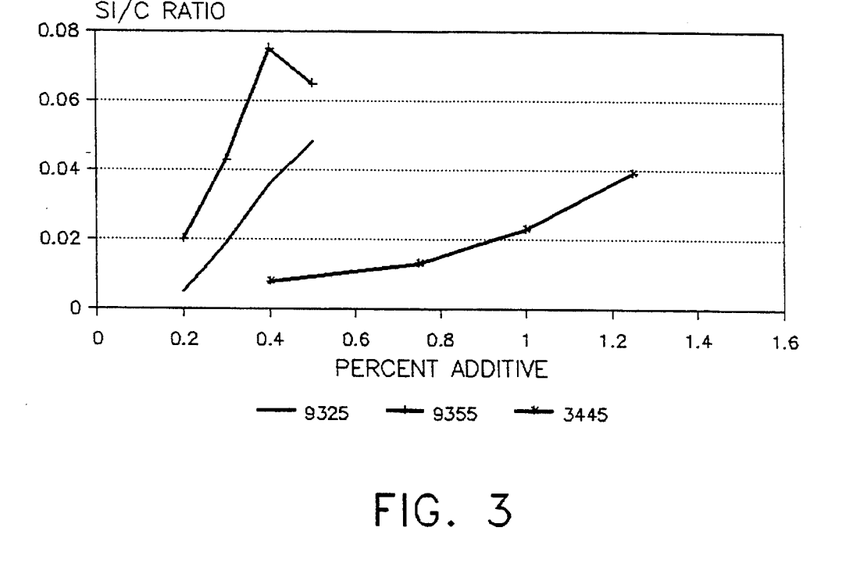
FIG. 3 is a plot of Si/C ratio versus additive concentration for two thermoplastic block copolymers having different levels of polyethylene blocks and a polypropylene homopolymer control.

FIG. 3 is a plot (line graph) of Si/C ratio versus additive concentration for two thermoplastic block copolymers having different levels of polyethylene blocks and a polypropylene homopolymer control. The figure was prepared from the data in Table 1 for Examples 1–12. The effects of both additive level and polymer type (the presence and/or level of polyethylene blocks) on Si/C ratios are clearly shown.

Figure 4:
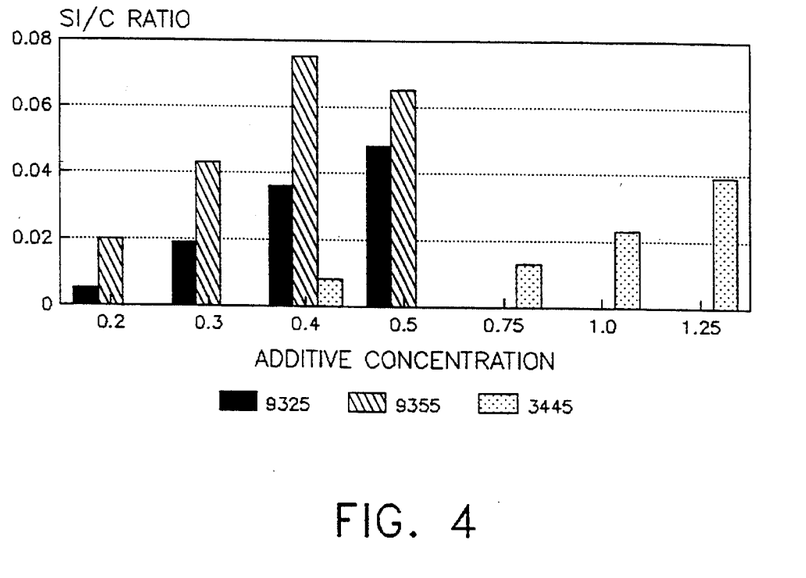
FIG. 4 is a bar graph of the data used to prepare FIG. 3 which emphasizes differences in Si/C ratios at given additive concentrations.

FIG. 4 is a bar graph of the data used to prepare FIG. 3 which emphasizes differences in Si/C ratios at given additive concentrations. The use of a bar graph rather than a line graph illustrates both the high Si/C ratios obtained with lower levels of additives and the pronounced increases in Si/C ratios which result from an increase in the level of polyethylene blocks.

Figure 5:
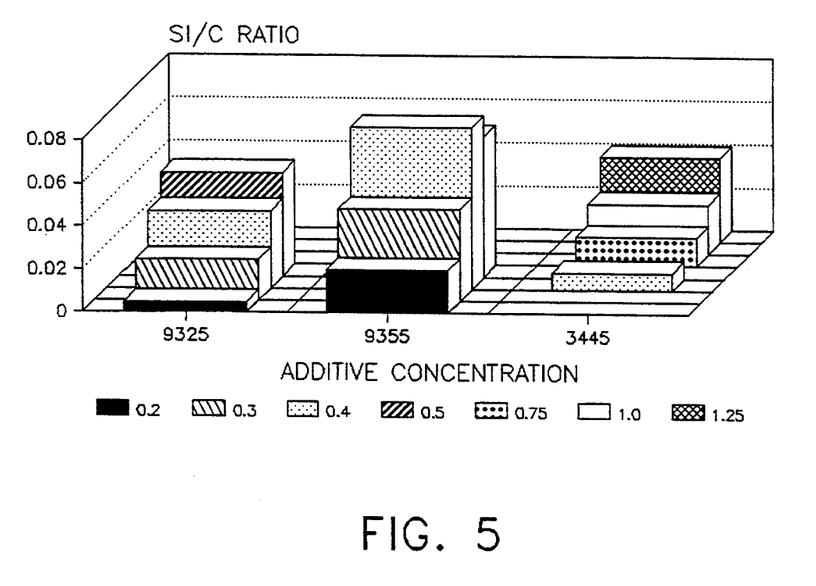
FIG. 5 is a three-dimensional bar graph of the data used to prepare FIG. 4, with the data being grouped by polymer type rather than additive concentration.

Finally, FIG. 5 is a three-dimensional bar graph of the data used to prepare FIG. 4, with the data being grouped by polymer type rather than additive concentration. The figure illustrates even more dramatically the features of the present invention illustrated by FIGS. 1–4.

Having thus described the invention, numerous changes and modifications thereof will be readily apparent to those having ordinary skill in the art without departing from the spirit or scope of the invention. For example, the compositions of the present invention also can contain fillers, delustrants, colorizers, stabilizers, pigments, and the like.

What is claimed is:

1. A surface-segregatable, melt-extrudable thermoplastic composition which comprises:

(A) a thermoplastic polypropylene-polyethylene block copolymer in which the polyethylene blocks constitute from about 1 to about 10 percent by weight of the copolymer; and (B) an additive having the general formula, in which:

(1) $R_1$–$R_7$ are independently selected monovalent $C_1$–$C_3$ alkyl groups;

(2) $R_8$ is hydrogen or a monovalent $C_1$–$C_3$ alkyl group;

(3) p represents an integer of from 0 to about 5;

(4) x represents an integer of from 1 to about 15;

(5) said additive has a weight average molecular weight of from about 350 to about 1,400; and (6) said additive is present in an amount of from about 0.1 to about 5 percent by weight, based on the amount of thermoplastic block copolymer.

2. The composition of claim 1, in which each of $R_1$–$R_7$ is a methyl group and $R_8$ is either hydrogen or a methyl group.

3. The composition of claim 1, in which p is either 1 or 2.

4. The composition of claim 3, in which p is 2.

5. The composition of claim 1, in which x is either 7 or 8.

6. The composition of claim 1, in which said additive has a weight average molecular weight of from about 350 to about 850.

7. The composition of claim 8, in which said additive is present in an amount of from about 1.0 to about 0.1 percent by weight, based on the amount of thermoplastic block copolymer.

* * * * *